United States Patent
Shaker et al.

(10) Patent No.: US 10,048,703 B1
(45) Date of Patent: Aug. 14, 2018

(54) FORCE FEEDBACK PRESSURE CUFF SYSTEMS AND METHODS

(71) Applicants: Adam Shaker, King George, VA (US); Andrew Czop, Alexandria, VA (US); Aaron O'Toole, Indian Head, MD (US); Carlos Ramos Garcia, King George, VA (US)

(72) Inventors: Adam Shaker, King George, VA (US); Andrew Czop, Alexandria, VA (US); Aaron O'Toole, Indian Head, MD (US); Carlos Ramos Garcia, King George, VA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 625 days.

(21) Appl. No.: 14/120,577

(22) Filed: Jun. 6, 2014

(51) Int. Cl.
G05D 16/20 (2006.01)

(52) U.S. Cl.
CPC ................... G05D 16/20 (2013.01)

(58) Field of Classification Search
CPC ....................................................... G05D 16/20
See application file for complete search history.

(56) References Cited

U.S. PATENT DOCUMENTS

| | | | | |
|---|---|---|---|---|
| 4,795,296 A * | 1/1989 | Jau | ................ | B25J 13/02 244/223 |
| 4,808,187 A * | 2/1989 | Patterson | ................ | A61F 2/72 623/25 |
| 5,282,722 A * | 2/1994 | Beatty | ................ | B05B 12/085 417/15 |
| 5,579,776 A * | 12/1996 | Medero | ................ | A61B 5/0225 600/493 |
| 5,888,213 A * | 3/1999 | Sears | ................ | A61F 2/68 623/24 |
| 5,941,828 A * | 8/1999 | Archibald | ................ | A61B 5/02116 600/494 |
| 7,117,136 B1 | 10/2006 | Rosedale | | |
| 2002/0191011 A1 | 12/2002 | Rasouli | | |
| 2011/0131839 A1* | 6/2011 | Ballin | ................ | A43B 13/186 36/141 |
| 2011/0238107 A1* | 9/2011 | Raheman | ................ | A61B 5/412 606/202 |
| 2011/0302694 A1 | 12/2011 | Wang et al. | | |
| 2012/0022415 A1* | 1/2012 | Mullen | ................ | A61H 9/0078 601/150 |
| 2014/0320392 A1* | 10/2014 | Chizeck | ................ | G06F 3/016 345/156 |

FOREIGN PATENT DOCUMENTS

WO    WO 2013063394    5/2013

* cited by examiner

*Primary Examiner* — Thomas C Lee
*Assistant Examiner* — Tri T Nguyen
(74) *Attorney, Agent, or Firm* — Fredric J. Zimmerman (57) ABSTRACT

A force feedback cuff system, method, and apparatus may include receiving force feedback signal from an external, remotely controlled device; processing the force feedback signal to determine a correlated amount of pressure; applying a correlated signal to air pump equipment to inflate or deflate an inflatable cuff on an operator; and continuing the receiving, processing, and applying while the operator controls the external, remotely controlled device to provide haptic feedback to the operator in an intuitive and non-obtrusive fashion.

19 Claims, 4 Drawing Sheets

FORCE FEEDBACK PRESSURE CUFF SYSTEMS AND METHODS

STATEMENT OF GOVERNMENT INTEREST

The present invention described herein may be manufactured and used by or for the Government of the United States of America for government purposes without the payment of any royalties thereon or therefore.

FIELD OF THE DISCLOSURE

The present disclosure relates generally to force feedback systems and methods. More particularly, the present disclosure relates to force feedback pressure cuffs that take generated force information gathered by sensors on one end of a system and relay that information back to the operator of the system in an intuitive fashion.

BACKGROUND OF THE DISCLOSURE

With respect to remotely controlled devices, there is a need to relay back information to operators. For example, applications may include robotic tele-operation for EOD Unmanned Ground Vehicles (UGVs), general military robotic platforms or manipulators, medical manipulators, personal gaming systems, medical prosthetics and the like. Conventionally, feedback is typically video and audio, and sometimes, physical feedback may be included, so-called force feedback or haptic technology. Haptic technology, or haptics, is a tactile feedback technology which takes advantage of the sense of touch by applying forces, vibrations, or motions to the user. This mechanical stimulation may be used to assist in the creation of virtual objects in a computer simulation, to control such virtual objects, and to enhance the remote control of machines and devices (tele-robotics). Haptic devices may incorporate tactile sensors that measure forces exerted by the user on the interface. Conventional haptic devices may use vibrations directed to an operator's hands or the like. There is a need for a more intuitive apparatus and method for conveying force feedback.

Conventionally, there are a number of ways to collect force feedback information at the remotely controlled end and relay them back to the operator. Some of the other known ways to provide this force feedback to the operator are visual, vibrations at an input controller, joystick controllers applying a corresponding force, and puppet controllers applying a corresponding force.

First, force feedback may include displaying some type of graphical depiction of the force applied at the remotely controlled end. For example, a colored slider bar that moves from one end to the other correlated to the amount of force applied on the other end. This method requires the operator to divert his attention from the task he is performing and periodically "check" the visual indicator to see if what he is inputting at the controller is being applied remotely. Splitting attention between display video and a visual indicator could cause the operator to miss something or extend the length of time a particular remote task takes. If there are multiple force feedback sensors relaying information back to the operator simultaneously, the cognitive burden to watch multiple graphics on top of a video display increases substantially.

A vibrating hand controller is another method used to relay force feedback information to the operator. The intensity of these vibrations correlate to the amount of force applied at the remotely controlled end. This controller is typically used to tele-operate various functions of the remote system. One of the major drawbacks of this approach is desensitization. Since so many tasks are demanded of the operator using his hands, it may become difficult to pick up on various levels of intensity of vibrations. In addition, this force feedback method is completely tied to the input controller, where using a different control method means losing the ability to receive force feedback (or develop a different way to pass it through). Another drawback is that this method does not lend itself very well to tele-operating multiple systems that support force feedback, such as dual arm manipulators (or grippers on the manipulators) aboard a robotic platform. Using one hand controller would be difficult to output force feedback and intensity of that force from both manipulators.

Haptic feedback joysticks exist that exert a retarding force opposite the direction that the operator is commanding. With this approach, typically the more force that is exerted at the remote end (for example with a manipulator lifting a weight) is translated back to the user, pushing back in the opposite direction or not allowing joystick movement past a certain point. One drawback to this approach is it not scalable, and may be interpreted differently from user to user. It also may be difficult to pick up on force feedback because of the burden already induced on the operator as it is a control mechanism first. In other words it may suffer from desensitization while operating, making it less intuitive to use. As with other approaches, it is explicitly tied to a specific controller. Using a different input device means losing the ability to receive force feedback.

Puppet controllers typically refer to devices that mimic a remote device in degrees of freedom (of movement) and sometimes scaled link length. With this approach, the operator may move this puppet controller to a certain position and the remote platform will mimic that same orientation. With puppet controllers, you may also incorporate a scaled force resistance that corresponds to the resisting force the remote system sees. For example, with a puppet controller for a manipulator arm, "pinching" its puppet gripper fingers cause the remote manipulator to open or close. If the grippers grasp an object and it sends force feedback information back to the puppet controller, the operator feels resistance in pinching that gripper. One drawback to using this approach is that it works best with a one to one relationship, where the gripper force felt at the remote end is identical to that applied at the puppet controller gripper. If it is not 1:1, the force feedback becomes less intuitive to the operator. Similar to the vibrating controller, the force feedback is exclusively tied to this puppet controller. Using a different input device means losing the ability to receive force feedback. Another drawback is the added complexity of using multiple force feedback systems simultaneously, such as with dual arm manipulators aboard a robotic platform. The cognitive load for the operator may be significantly higher controlling so many inputs (and receiving force feedback information) at once.

BRIEF SUMMARY OF THE DISCLOSURE

In an exemplary embodiment, a force feedback cuff system includes air pump equipment coupled to a wearable, inflatable cuff; system inputs coupled to an external, remotely controlled device to receive force feedback signals therefrom indicative of force associated with the external, remotely controlled device; user controls for selectively determining operating conditions; and a microcontroller coupled to the air pump equipment, the system inputs, and the user controls, where the microcontroller is programmed to selectively inflate or deflate the wearable, inflatable cuff by controlling the air pump equipment based on the force feedback signals and the operating conditions. The force feedback cuff system may further include a module housing for the air pump equipment, the system inputs, the user controls, and the microcontroller, where the wearable, inflatable cuff connects to the air pump equipment via an air pressure output port on the module housing. The operating conditions may include a scale setting such that pressure to the wearable, inflatable cuff builds up from zero up to a maximum scale setting.

The operating conditions may include a plurality of adjustable scale settings such that varying ranges of forces experienced by the external, remotely controlled device are felt by an operator wearing the wearable, inflatable cuff. Generally, the ranges may be programmed and may be selected to vary based on the specific needs. Further, a linear or a non-linear relationship may be programmed between the sensor output and the pressure generated at the cuff. Force feedback correlated to force experienced by the external, remotely controlled device may be relayed via the wearable, inflatable cuff independent of a controller used by an operator of the external, remotely controlled device. The wearable, inflatable cuff may be worn by an operator of the external, remotely controlled device on one of a forearm, a wrist, a bicep, a leg, and an ankle. The air pump equipment may include an air pump; an air pressure output port coupled to the wearable, inflatable cuff; and a solenoid between the air pump and the air pressure output port. The wearable, inflatable cuff may include a fabric configured to be selectively secured radially on a body part of an operator; and an inflatable air bladder on an interior of the fabric configured to be selectively inflated and deflated by the air pump equipment. The air pump equipment, the system inputs, the user controls, and the microcontroller are integrated in the wearable, inflatable cuff. The wearable, inflatable cuff may relay force experienced by the external, remotely controlled device as a radial pressure applied by the inflatable air bladder to the body part. Two exemplary external, remotely controlled devices may include a gripper on a robot arm manipulator or a prosthetic device, e.g., a prosthetic hand.

In another exemplary embodiment, a force feedback cuff method includes receiving force feedback signal from an external, remotely controlled device; processing the force feedback signal to determine a correlated amount of force; applying a correlated signal to air pump equipment to inflate or deflate an inflatable cuff on an operator; and continuing the receiving, processing, and applying while the operator controls the external, remotely controlled device to provide haptic feedback to the operator in an intuitive and non-obtrusive fashion. The force feedback cuff method may include securing the inflatable cuff to a body part of the operator; and controlling the external, remotely controlled device via a controller while receiving force feedback via the inflatable cuff related to the controlling. The force feedback correlated to force experienced by the external, remotely controlled device may be relayed via the inflatable cuff independent of the controller used by the operator of the external, remotely controlled device. The force feedback cuff method may further include adjusting a scale setting of the correlated signal such that pressure to the inflatable cuff builds up from zero up to a maximum scale setting.

In yet another exemplary embodiment, a force feedback cuff apparatus includes an air pump; an air pressure output port coupled to an air hose; a solenoid between the air pump and the air pressure output port; a microcontroller coupled to the solenoid; system inputs coupled to the microcontroller and configured to receive force feedback signals from a remote device. The microcontroller is programmed to control, selectively, the solenoid to provide air pressure to the air hose and an associated inflatable cuff connected to the air hose based on the force feedback signals from the system inputs and operating conditions set by an operator. The operating conditions may include a scale setting such that pressure to the inflatable cuff builds up from zero up to a maximum scale setting. The operating conditions may include a plurality of adjustable scale settings such that varying ranges of forces experienced by the remote device are felt by the operator wearing the inflatable cuff. Force feedback may be correlated to force experienced by the remote device is relayed via the inflatable cuff independent of a controller used by the operator of the remote device. The inflatable cuff may be worn by the operator of the remote device on one of a forearm, a wrist, a bicep, a leg, and an ankle.

BRIEF DESCRIPTION OF THE DRAWINGS

The present disclosure is illustrated and described herein with reference to the various drawings, in which like reference numbers are used to denote like system components/method steps, as appropriate, and in which.

DETAILED DESCRIPTION OF THE DISCLOSURE

In various exemplary embodiments, the present disclosure relates to a force feedback cuff system (system) and, in particular, a force feedback pressure cuff takes generated force information gathered by sensors on one end of an external device and relays that information back to the operator in an intuitive fashion. In an exemplary embodiment, the purpose of the force feedback pressure cuff is to create a unique and novel way to take generated sensor output(s), for example, force, pressure, torque and other information, gathered by at least one sensor on one end of an external device (for example a tele-operated robotic platform), and relay that information as a system input(s) back to the operator in an intuitive fashion. For clarification, the sensor output(s) is the same as the system input(s). In another exemplary embodiment, two or more sensors are used. This force feedback device is intended to give the operator better situational awareness through enhanced telepresence. The Force Feedback Pressure Cuffs utilize a received signal from one or more sensors on an external device and apply a corresponding force to a cuff (i.e., a cuff similar to a blood pressure monitor) to provide feedback to an operator. In an exemplary embodiment, a single sensor, such as a force transducer, provides the system inputs. In another exemplary embodiment, two or more sensors may be used to provide the system inputs, for example, one sensor may measure force exerted at a robot gripper and a second sensor may measure an amount of torque induced by the gripper wrist. Further, force feedback is needed in remote operator environments as generally only visual and audio feedback is provided. Conventional force feedback systems generally apply force to hands (e.g., computer game controllers) whereas the present disclosure seeks to apply the force to the wrist, bicep, etc. Various applications are contemplated from remote robotic operators to medical applications and the like.

Figure 1:
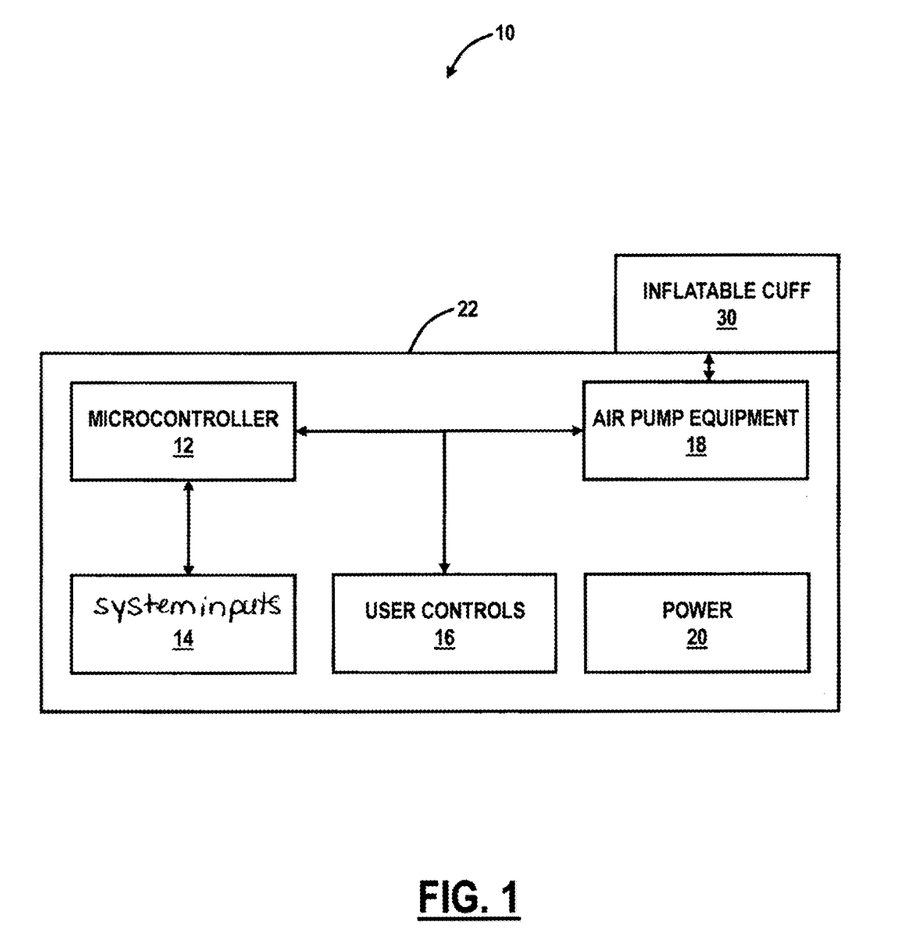
FIG. 1 is a block diagram of a force feedback cuff system in accordance with some exemplary embodiments.

Referring to FIG. 1, in an exemplary embodiment, a block diagram illustrates a force feedback cuff system 10. The force feedback cuff system 10 includes a microcontroller 12, a system interface structure for receiving sensor outputs, which now become system inputs (system inputs) 14, user controls 16, air pump equipment 18, power 20, a module housing 22, and an inflatable cuff 30. The module housing 22 contains the microcontroller 12, the system inputs via the system interface structure 14, the user controls 16, the air pump equipment 18, and the power 20. It should be appreciated by those of ordinary skill in the art that FIG. 1 depicts the force feedback cuff system 10 in an oversimplified manner, and a practical embodiment may include additional components and suitably configured processing logic to support known or conventional operating features that are not described in detail herein.

The microcontroller 12 is hardware device for executing software/firmware instructions. The microcontroller 12 may be any custom made or commercially available processor, a central processing unit (CPU), an auxiliary processor among several processors associated with the force feedback cuff system 10, a semiconductor-based microprocessor (in the form of a microchip or chip set), or generally any device for executing software instructions. When the force feedback cuff system 10 is in operation, the microcontroller 12 is configured to execute software/firmware stored therein, to communicate data to and from the system inputs 14, the user controls 16, and the air pump equipment 18, and generally to control operations of the force feedback cuff system 10 pursuant to the software/firmware instructions. In an exemplary embodiment, the force feedback cuff system 10 may include a mobile optimized hardware device such as optimized for power consumption. In another exemplary embodiment, the microcontroller 12 may be preprogrammed to implement various functions associated with the force feedback cuff system 10.

The system inputs 14 are communicatively coupled to an external, remotely controlled device (not shown) to receive force feedback signals. The system inputs 14 may include, for example, a serial port, a parallel port, a small computer system interface (SCSI), a serial ATA (SATA), a fibre channel, Infiniband, iSCSI, a PCI Express interface (PCI-x), an infrared (IR) interface, a radio frequency (RF) interface, and/or a universal serial bus (USB) interface. Other embodiments are also contemplated. The system inputs 14 are configured to receive some real-time indicator of force being applied at the external, remotely controlled device, such as, for example, in pound force. In an exemplary embodiment, the system interface structure for receiving the sensor outputs, which become system inputs, 14 may include a bulkhead serial connector.

The user controls 16 enable an operator to configure and operate the force feedback cuff system 10. For example, the user controls 16 may be any type of user input for the user to manipulate on the module housing 22. The user controls 16 may include a power switch for selectively enabling and disabling the force feedback cuff system 10 and a scale selection mechanism. The scale selection mechanism may be a switch, dial, etc. which determines a force multiplier to apply to the inflatable cuff 30. This scale selection is a scaling factor which may be adjusted. For example, if the external, remotely controlled device is experiencing small amounts of force or small changes in force, the scale selection mechanism may be adjusted higher so it may be felt by the operator. Conversely, if the external, remotely controlled device is experiencing large amounts of force or large changes in force, the scale selection mechanism may be adjusted lower. The user controls 16 are connected to the microcontroller 12 and the air pump equipment 18. For example, the user controls 16 may provide the scaling factor to the microcontroller 12 and/or the air pump equipment 18 for settings based thereon. As previously indicated, generally, the ranges may be programmed and may be selected to vary based on the specific needs. Further, a linear or a non-linear relationship may be programmed between the sensor output and the pressure generated at the cuff. In an exemplary embodiment, the constriction pressure is in a range from 0-10 pounds per square inch (psi) (max). The cuff is similar to this pressure range output where the exact range is not necessarily important outside of safety and comfort. As discussed below, and in an exemplary embodiment, three sensor output ranges were programmed into a prototype: a 2 pound force (max), a 30 pound force (max) and a 75 pound force (max). Based on the sensor output ranges, the cuff provided a constricting pressure of 0-10 psi scaled from a minimum to a maximum of the sensor output. Accordingly, greater sensitivity occurred when the scale was set to a 2 pound force for squeezing/picking up lighter weight objects, whereas a large scale was needed when picking up heavy objects and greater range was needed with less sensitivity. A medium setting, for example, of a 30 pound force, balanced range and sensitivity.

The air pump equipment 18 includes various hardware configured to inflate, selectively, and deflate the inflatable cuff 30. The air pump equipment 18 are connected to the inflatable cuff 30 via an air hose and to the microcontroller 12 for receiving instructions. For example, the air pump equipment 18 may include an air pump, a solenoid controlling the rate of air pressure bleed-off from the system, and the like. Generally, the air pump equipment 18 are configured to inflate/deflate the inflatable cuff 30 based on a determined amount of force feedback by the microcontroller 12 based on force feedback signals from the system inputs 14 as well as based on a scaling factor from the user controls 16. The air pump equipment 18 could also include a pressure sensor to monitor (for accuracy purposes), and potentially a safety bleed-off sensor so that there is no danger of over constriction.

The power 20 includes power components to power the microcontroller 12, the system inputs 14, the user controls 16, and the air pump equipment 18. The power 20 may include a battery (rechargeable and/or replaceable), an AC/DC power unit, and the like. The power 20 could also be used to power an external display to relay system status or other state.

Figure 2:
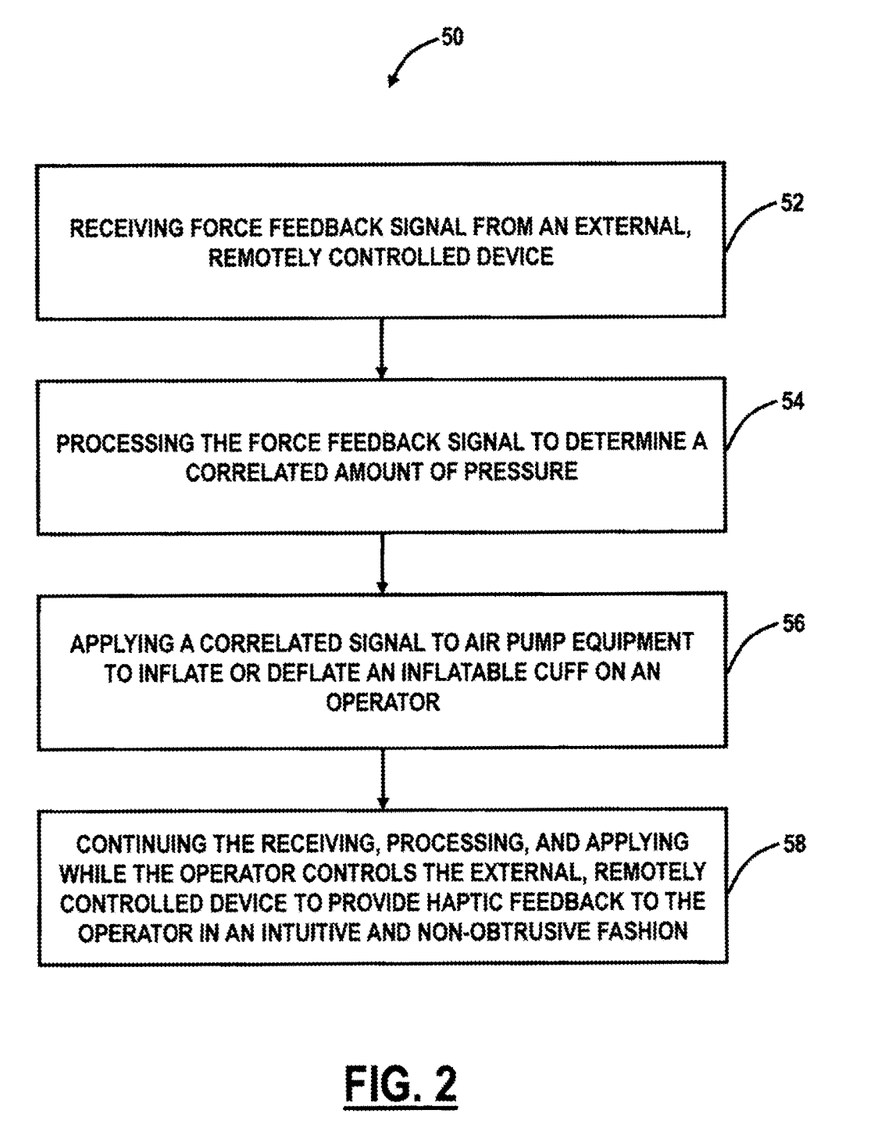
FIG. 2 is a flowchart illustrates a force feedback cuff method in accordance with some exemplary embodiments.

Referring to FIG. 2, in an exemplary embodiment, a flowchart illustrates a force feedback cuff method 50. The force feedback cuff method 50 may be implemented with the force feedback cuff system 10 or the like. The force feedback cuff method 50 may be utilized by an operator to receive intuitive and non-obtrusive force feedback while controlling an external, remote device. For example, the external, remote device may be a dual arm manipulator on a robot, and the force feedback may be pressure applied by an inflatable cuff on the operator's forearm, wrist, or bicep indicative of a corresponding pressure being applied by the dual arm manipulator. Further, the force feedback cuff method 50 may be implemented with multiple cuffs on an operator, e.g. on both arms to simulate dual arms of a robot. Also, the external, remote device may be a prosthetic arm with force feedback capability where the force feedback cuff system worn on the wearer's upper arm or shoulder apply a corresponding pressure indicative of the forces the prosthetic hand apply to various objects or other surfaces. Other embodiments are also contemplated.

The force feedback cuff method 50 includes receiving force feedback signal from an external, remotely controlled device (step 52). The external, remotely controlled device may be any device that is operator controlled and exerts some force by which the force feedback cuff method 50 may physically relay an indication of the force to the operator. In an exemplary application, the force may be a gripping force since the inflatable cuff may indicate the same type of force to the operator, i.e. how much pressure is asserted on the inflatable cuff correlates to how much pressure the gripping force of the external, remotely controlled device is being applied. Of course, the force may be other types of force besides the gripping force, e.g. pulling, pushing, and combinations thereof. The force feedback cuff method 50 may model any type of force that the external, remotely controlled device is experiencing and/or applying. Again, the force feedback signal is indicative of such force.

The force feedback cuff method 50 includes processing the force feedback signal to determine a correlated amount of pressure (step 54). The force feedback signal provides an indication of current force being experienced by the external, remotely controlled device. The force feedback signal may be processed by a microcontroller or general processing device to determine the present value, the delta from previous values, and corresponding settings for inflating or deflating the inflatable cuff. For example, if the force feedback signal is relatively constant, the processing may determine no changes are needed to the inflatable cuff. If the force feedback signal indicates an increase in force, the processing may determine the inflatable cuff needs to be inflated more to provide more pressure. Finally, if the force feedback signal indicates a decrease in force, the processing may determine the inflatable cuff needs to be deflated more to relieve some pressure. Generally, the processing is to determine a correlated amount of pressure for the inflatable cuff based on the force feedback signal. Note, the operator output may never exceed a certain pressure for safety, i.e. the constricting pressure may not keep increasing with the correlated force feedback inputs. The user output is scaled in an intuitive fashion across this force feedback range. The maximum pressure may depend on a number of factors, including exposure time, surface area applied to, geometry of the bladder and where the force is applied on the body. In an exemplary embodiment, the experimental maximum pressure was about 9.5 psi.

The force feedback cuff method 50 includes applying a correlated signal to air pump equipment to inflate or deflate an inflatable cuff on an operator (step 56). The correlated signal may be determined by the processing and may be indicative of the correlated amount of force for the inflatable cuff based on the force feedback signal. Here, the microcontroller or general processing device is instructing the inflation or deflation of the inflatable cuff. Finally, the force feedback cuff method 50 includes continuing the receiving, processing, and applying while the operator controls the external, remotely controlled device to provide haptic feedback to the operator in an intuitive and non-obtrusive fashion (step 58). An advantage of the force feedback cuff method 50 is that it provides force feedback in a more intuitive fashion, i.e. radial pressure applied or relieved by the inflatable cuff, as opposed to conventional vibration methods. Another advantage of the force feedback cuff method 50 is that it avoids the hands, i.e. is non obtrusive, as the inflatable cuff is away from the hands. This feature is important as hand-based force feedback may distract or interrupt the operator as well as become desensitized. Of note, the inflation and deflation (or bleed-off) of the cuff needs to happen quickly for the force feedback to be intuitive. In particular, "quickly" means that if there is too much latency in the system (force output to cuff pressure output), then the system is no longer intuitive. In an exemplary embodiment, an approximate threshold for latency that a human can tolerate is about 200 milliseconds where a latency greater than 200 milliseconds the commands become noticeably delayed. Note, the size of a bladder in the inflatable cuff is selected so that the pump and solenoid would fill and bleed-off fast, otherwise, there could be latency and it becomes less intuitive for real-time (or near real-time use). Generally, the larger the air bladder being filled, then the larger the air pump must be (or more air it must put out) along with the solenoid building or bleeding off pressure.

Figure 3:
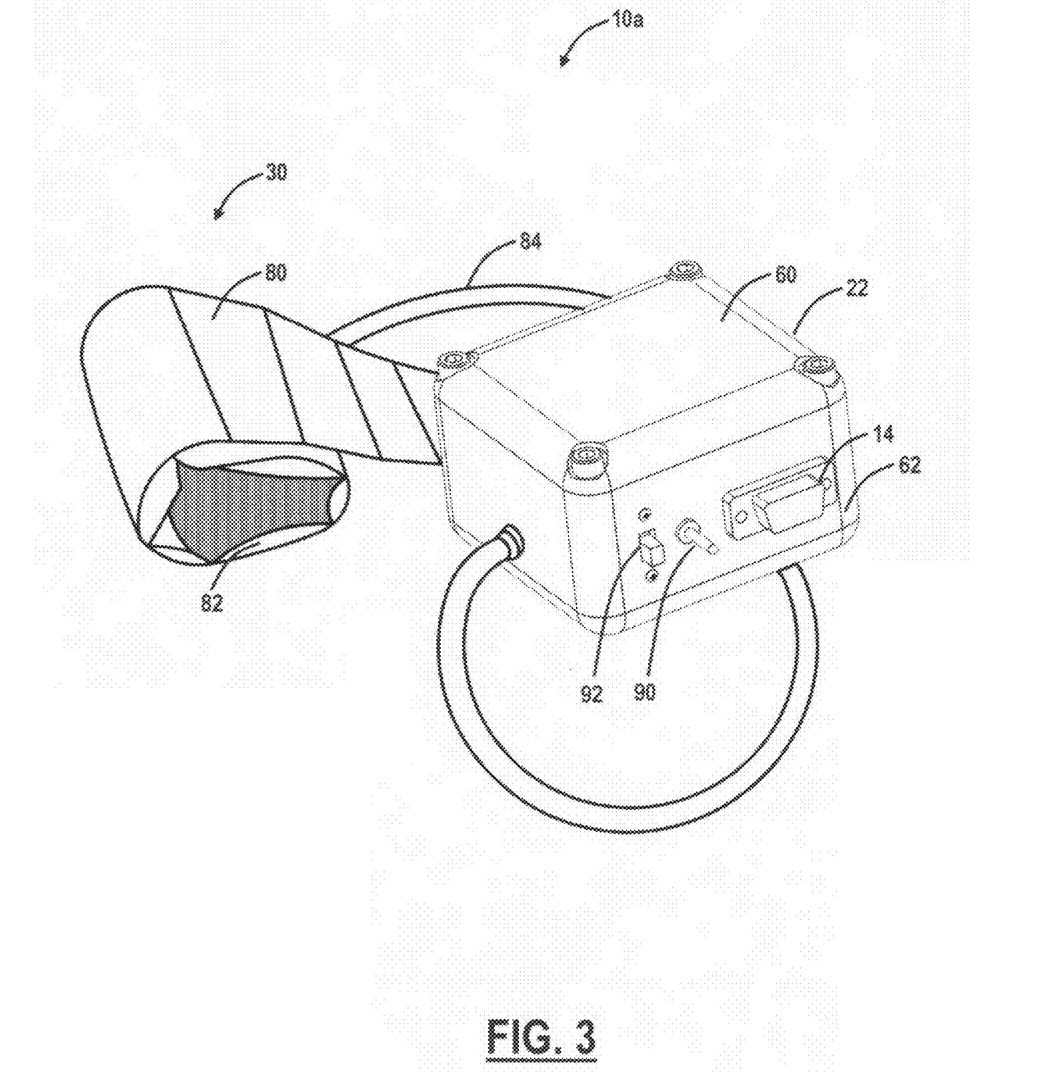
FIG. 3 is a perspective view of the module housing connected to the inflatable cuff.
Figure 4:
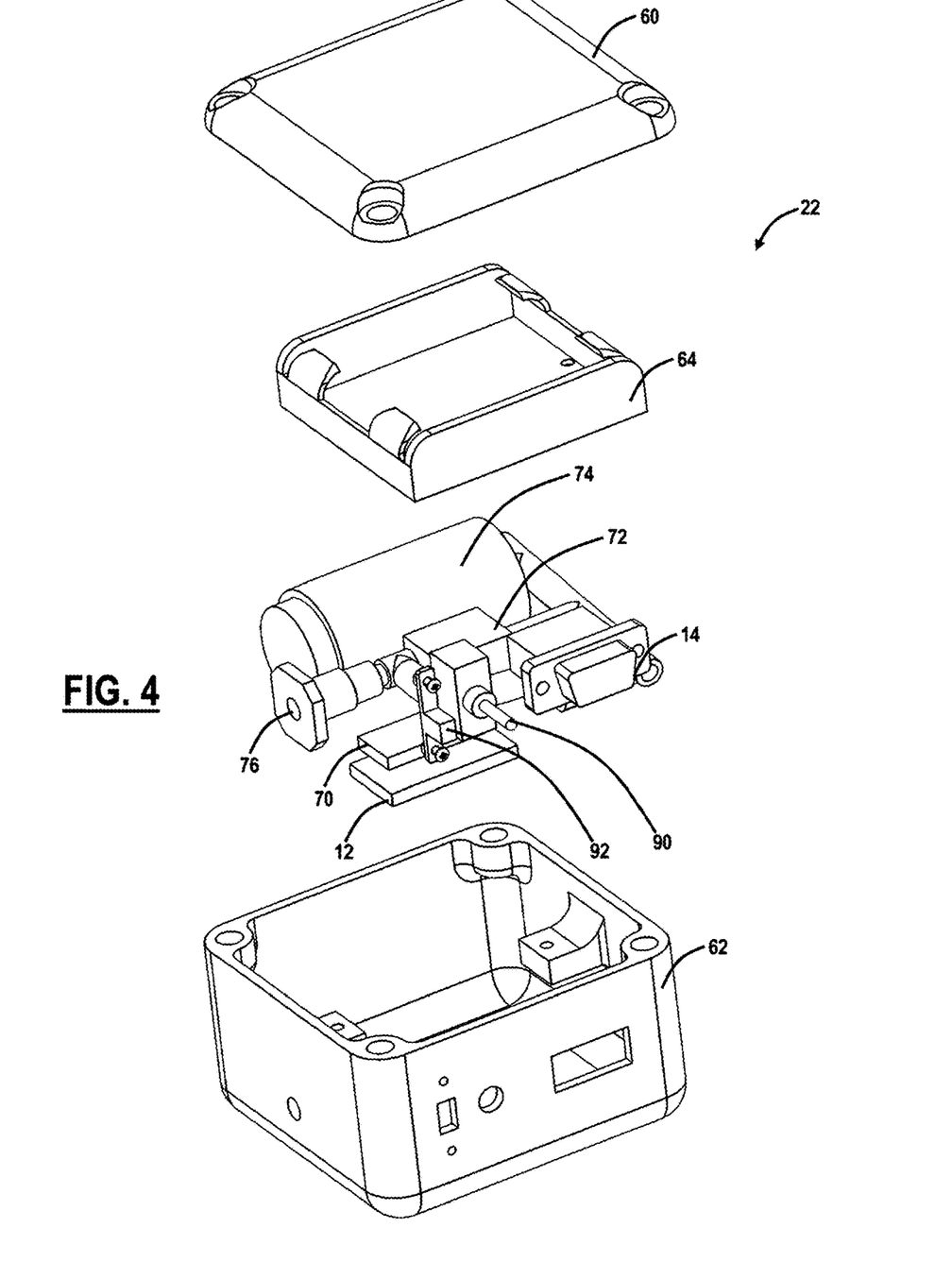
FIG. 4 is an interior view of the module housing and associated components contained therein.

Referring to FIGS. 3 and 4, in exemplary embodiments, perspective views illustrate an exemplary embodiment of a force feedback cuff system 10*a*. FIG. 3 is a perspective view of the module housing 22 connected to the inflatable cuff 30, and FIG. 4 is an interior view of the module housing 22 and associated components contained therein. The force feedback cuff system 10*a* is presented for illustration purposes and those of ordinary skill in the art will recognize other practical exemplary embodiments could be implemented for the force feedback cuff system 10 and the force feedback cuff method 50.

In an exemplary embodiment, the module housing 22 may be an enclosure measuring approximately 3" wide×3.25" long×2.25" tall. The system interface structure for receiving sensor outputs, which become system inputs, 14 may include a bulkhead serial connector (other input mechanisms may also be used), to receive some type of sensor output from the external, remotely controlled device, e.g. force feedback data in pound force. The module housing 22 may include a cover 60 that may be affixed to, attached to, or disposed to a bottom portion 62. In an exemplary embodiment, the cover 60 may be selectively removable to replace batteries housed in a battery enclosure 64. In another exemplary embodiment, the components in the module housing 22 may be integrated on or attached to the inflatable cuff 30.

Some type of sensor output (force feedback data, for example pound force) is provided as the system input, that is, the same data, 14 via a bulkhead serial connector (although there is no reason another input mechanism could not be used), to a logic converter 70 as indicated in FIG. 4 and a preprogrammed microcontroller 12. The microcontroller 12 may be easily modified to accept a number of different types of inputs from the system inputs 14. The input is converted to a Pulse Width Modulation (PWM) signal, which varies with the force input.

This PWM drives a solenoid 72, which acts to produce pressure in the force feedback cuff system 10*a* (i.e., the solenoid's valve is nominally open, and closes when power is applied to it). At the same time, a DC motor/air pump 74 is providing constant air pressure. This pressure produced by the DC motor/air pump 74 is only allowed to build up when the solenoid 72 is closed. The air pressure is provided through an air pressure output port 76 located after the solenoid 72 and the DC motor/air pump 74.

The operator input is the inflatable cuff 30 worn on either the wrist, forearm, bicep, leg, ankle, etc. The inflatable cuff 30 is configured to be worn radially around a part of the operator's body. The inflatable cuff 30 may be made of a fabric 80 on an outside and an air bladder 82 on an inside portion. The fabric 80 may be selectively sized and secured via a fabric hook and loop fastener (e.g., Velcro®). The air bladder 82 is connected via an air hose 84 to the module housing 22 at the air pressure output port 76 (i.e., the inflatable cuff 30 connects to the air pump equipment 18) as indicated in FIG. 4. The air bladder 82 inside the fabric 80 quickly inflates as the pressure increases and quickly deflates as pressure decreases from the air pump equipment 18. The air bladder 82 does not need to wrap around the user (e.g., wrist); the fabric 80 does however. The air bladder 82 needs to inflate and deflate rapidly in order to provide radial constriction using a small localized bladder attached to the fabric 80. By minimizing the time to inflate and deflate the pressure cuff, the haptic feedback is real-time or near-real time as a means to make the device as intuitive as possible.

The module housing 22 is designed to be flexible across a variety of objects, and incorporates an external switch 90 designed to allow the operator to select one of three preset scales for the trigger points of the input force. For example, in an exemplary embodiment, the first switch position is set to 2 pound force, the second to 30 pound force, and the third to 75 pound force. These scales are preprogrammed on the microcontroller 12 and may be easily modified. The scales indicate the max force before the PWM tells the solenoid 72 to remain closed and hold max pressure.

The intuitive part of this haptic feedback is that pressure gradually builds from the minimum (0 pounds in this case) to the maximum of each scale (2, 30, 75). This means there is increased sensitivity at 2 pounds and it is geared toward grasping lighter or more delicate objects, versus the sensitivity at 75 pounds where the operator will "feel" the induced pressure building more slowly as the grasping force rises from 0 to 75 pounds. The module housing 22 may be powered internally by 4 AA size batteries configured to provide ~6V and located in the battery enclosure 64. There is also an external power switch 92 to turn it on and off.

Again, using force feedback via the force feedback cuff system 10, 10*a* and the force feedback cuff method 50 allows the operator of a remote platform to gain better situational awareness of the surrounding environment. In the case of force feedback coupled to grip force on a robotic manipulator, it gives the operator the ability to "feel" how firm the gripper is gasping an object in a given workspace. This tactical feel may be extremely useful in a number of environments. Generally, the primary feedback to the operator is a video camera feed that shows one or multiple views of the environment. Some instances where video display alone may not be sufficient are: low light environments, when the camera perspective or view is not ideal, when the sun causes a glare in the camera lens or coming off an object, or even when the object being manipulated does not noticeably deflect (rigid objects).

This haptic user input of the force feedback cuff system 10, 10*a* and the force feedback cuff method 50 is a unique and novel approach to relay force feedback information intuitively to the operator. Some major advantages of this type of approach over other approaches are that it is controller agnostic and hands free. This means it may be used with virtually any control device (joysticks, hand controllers, etc.) and may be worn on either hand, arm, wrist, bicep, leg, ankle, etc. making it a very feasible option when using a dual arm system where an operator's hands are the primary input to a control scheme, but more than one force feedback input needs to be provided back to the operator. The position of the pressure provided is remoted away from the operator's hands, where otherwise a haptic input may have increased the burden on the operator or overwhelmed his ability to differentiate haptic inputs from the system. The form factor of the module is relatively small when compared to other haptic feedback devices, and allows the operator to disconnect, quickly, from the module by unstrapping the Velcro® wrist cuff.

This prototype includes the ability to accept an input from a varying number of external sensors and produce and output force to the operator. The developed prototype includes a microcontroller, a logic converter, miniature air pump, miniature solenoid, air hosing, internal battery, power switch, and three position scale selection switch.

In the various exemplary embodiments described herein, the inflatable cuff has been shown apart from a module, connected via an air hose. In another exemplary embodiment, the force feedback cuff system 10, 10*a* and the force feedback cuff method 50 could be an integrated device where air compressor, electronics, etc. are all built into the inflatable cuff (without hoses). This integrated version could communicate to the remote device wirelessly or via aforementioned communication mechanisms, i.e. the system inputs 14 could be wireless and the various components described herein are integrated into the inflatable cuff 30. This configuration would remove the air hose as a distraction for the operator.

It will be appreciated that some exemplary embodiments described herein may include one or more generic or specialized processors ("one or more processors") such as microprocessors, digital signal processors, customized processors, and field programmable gate arrays (FPGAs) and unique stored program instructions (including both software and firmware) that control the one or more processors to implement, in conjunction with certain non-processor circuits, some, most, or all of the functions of the methods and/or systems described herein. Alternatively, some or all functions may be implemented by a state machine that has no stored program instructions, or in one or more application specific integrated circuits (ASICs), in which each function or some combinations of certain of the functions are implemented as custom logic. Of course, a combination of the aforementioned approaches may be used. Moreover, some exemplary embodiments may be implemented as a non-transitory computer-readable storage medium having computer readable code stored thereon for programming a computer, server, appliance, device, etc. each of which may include a processor to perform methods as described and claimed herein. Examples of such computer-readable storage mediums include, but are not limited to, a hard disk, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory), Flash memory, and the like. When stored in the non-transitory computer readable medium, software may include instructions executable by a processor that, in response to such execution, cause a processor or any other circuitry to perform a set of operations, steps, methods, processes, algorithms, etc.

Although the present disclosure has been illustrated and described herein with reference to exemplary embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following claims.

Finally, any numerical parameters set forth in the specification and attached claims are approximations (for example, by using the term "about") that may vary depending upon the desired properties sought to be obtained by the present invention. At the very least, and not as an attempt to limit the application of the doctrine of equivalents to the scope of the claims, each numerical parameter should at least be construed in light of the number of significant digits and by applying ordinary rounding.

What is claimed is:

1. A force feedback cuff system, comprising:
   air pump equipment being coupled to a wearable, inflatable cuff;
   a system interface structure providing system inputs being coupled to an external, remotely controlled device for receiving force feedback signals, which are sensor outputs, being associated with the external, remotely controlled device,
   wherein the sensor outputs are system inputs;
   user controls for selectively determining operating conditions; and
   a microcontroller being couple to the air pump equipment, the system inputs, and the user controls,
      wherein the microcontroller is programmed to select one of the inflation and deflation, as needed, of the wearable, inflatable cuff by controlling the air pump equipment based on the force feedback signals and the operating conditions,
      wherein the user controls include an adjustable scale setting mechanism with a scale setting, which determines a force multiplier to apply to the wearable, inflatable cuff,
      wherein the air pump equipment includes an air pump, an air pressure output port coupled to the wearable, inflatable cuff, and a solenoid valve, which is situated between the air pump and the air pressure output port,
      wherein the scale setting is a programmable scale setting, which includes a range of force settings, and wherein the range of force settings include one of a linear and a non-linear relationship between the sensor outputs, which are the system inputs, and air pressure generated at the wearable, inflatable cuff.

2. The force feedback cuff system of claim 1, further comprising a module housing including an inner portion for containing the air pump equipment, the system inputs, the user controls, and the microcontroller, wherein the wearable, inflatable cuff connects to the air pump equipment via an air pressure output port on the module housing.

3. The force feedback cuff system of claim 1, wherein the scale setting is such that pressure to the wearable, inflatable cuff builds up from zero up to a maximum scale setting.

4. The force feedback cuff system of claim 3, wherein the operating conditions comprise a plurality of adjustable scale settings such that varying ranges of force feedback signals experienced by the external, remotely controlled device are felt by an operator wearing the wearable, inflatable cuff.

5. The force feedback cuff system of claim 1, wherein force feedback correlated to force feedback signals experienced by the external, remotely controlled device is relayed via the wearable, inflatable cuff independent of a controller used by an operator of the external, remotely controlled device.

6. The force feedback cuff system of claim 1, wherein the wearable, inflatable cuff is worn by an operator of the external, remotely controlled device on one of a foreman, a wrist, a bicep, a leg, and an ankle.

7. The force feedback cuff system of claim 1, wherein the wearable, inflatable cuff comprises a fabric configured to be selectively secured radically on a body part of an operator, and an inflatable air bladder on an interior of the fabric configured to be selectively inflated and deflated as needed by the air pump equipment, and
   wherein the air pump equipment, the system inputs, the user controls, and the microcontroller are integrated in the wearable, inflatable cuff.

8. The force feedback cuff system of claim 7, wherein the wearable, inflatable cuff relays the force feedback signals experienced by the external, remotely controlled device as a radial pressure applied by the inflatable air bladder to the body part.

9. The force feedback cuff system of claim 1, wherein the force feedback cuff system is a hands free force feedback cuff system, and wherein the external, remotely controlled device comprises a robot arm manipulator.

10. The force feedback cuff system of claim 1, wherein the external, remotely controlled device comprises a prosthetic hand.

11. A force feedback cuff method, comprising:
    receiving a force feedback signal from an external, remotely controlled device;
    processing the force feedback signal for determining a correlated amount of a pressure;
    applying a correlated signal to air pump equipment for one of inflation and deflation, as needed, of an inflatable cuff on an operator; and
    continuing the receiving, the processing, and said applying while the operator is
    controlling the external, remotely controlled device for providing a haptic feedback to the operator in an intuitive and non-obtrusive fashion,
       wherein the force feedback signal includes a scaling factor from user controls for selectively determining operation conditions, wherein the user controls include an adjustable scale setting mechanism with a scale setting, which determines a force multiplier to apply to the wearable, inflatable cuff, and wherein the air pump equipment includes an air pump, an air pressure output port coupled to the wearable, inflatable cuff, and a solenoid valve, which is situated between the air pump and the air pressure output port,
       wherein the scale setting is a programmable scale setting, which includes a range of force settings, and wherein the range of force settings include one of a linear and a non-linear relationship between the sensor outputs, which are the system inputs, and air pressure generated at the wearable, inflatable cuff.

12. The force feedback cuff method of claim 11, further comprising securing the inflatable cuff to a body part of the operator; and controlling the external, remotely controlled device via a controller while receiving the haptic feedback via the inflatable cuff related to the controlling.

13. The force feedback cuff method of claim 12, wherein the force feedback signals experienced by the external, remotely controlled device are relayed via the inflatable cuff independent of the controller used by the operator of the external, remotely controlled device.

14. The force feedback cuff method of claim 11, further comprising adjusting the scale setting of the correlated signal such that pressure to the inflatable cuff is building up from zero up to a maximum scale setting.

15. A force feedback cuff apparatus, comprising:
an air pump;
an air pressure output port being coupled to an air hose;
a solenoid being situated between the air pump and the air pressure output port;
a microcontroller being coupled to the solenoid and user controls; and
a system interface structure providing system inputs being coupled to the microcontroller and being configured for receiving force feedback signals from a remote device,
wherein the microcontroller is programmed to control, selectively, the solenoid to provide air pressure to the air hose and an associated inflatable cuff,
wherein the associated inflatable cuff is connected to the air hose, based on the force feedback signals from the system inputs and operating conditions set by an operator,
wherein the user controls selectively determining operation conditions, and the user controls include an adjustable scale setting mechanism with a scale setting, which determines a force multiplier to apply to the inflatable cuff,
wherein the air pump equipment includes the air pump, an air pressure output port coupled to the inflatable cuff, and the solenoid valve,
wherein the scale setting is a programmable scale setting, which includes a range of force settings, and wherein the range of force settings include one of a linear and a non-linear relationship between the sensor outputs, which are the system inputs, and air pressure generated at the wearable, inflatable cuff.

16. The force feedback cuff apparatus of claim 15, wherein the operating conditions comprise the scale setting range where the air pressure to the inflatable cuff builds up from zero up to a maximum scale setting.

17. The force feedback cuff apparatus of claim 15, wherein the operating conditions comprise a plurality of adjustable scale settings such that varying ranges of force feedback signals experienced by the remote device are felt by the operator wearing the inflatable cuff.

18. The force feedback cuff apparatus of claim 15, wherein the force feedback signals experienced by the remote device are relayed via the inflatable cuff independent of a controller used by the operator of the remote device.

19. The force feedback cuff apparatus of claim 15, wherein the inflatable cuff is worn by the operator of the remote device on one of a forearm, a wrist, a bicep, a leg, and an ankle.

* * * * *